United States Patent
Muntendam

(10) Patent No.: US 12,397,005 B2
(45) Date of Patent: Aug. 26, 2025

(54) PHARMACEUTICAL COMPOSITIONS OF TORSEMIDE AND USES THEREOF

(71) Applicant: SQ Innovation AG, Zug (CH)

(72) Inventor: Pieter Muntendam, Boxford, MA (US)

(73) Assignee: SQ Innovation AG, Zug (CH)

( * ) Notice: Subject to any disclaimer, the term of this patent is extended or adjusted under 35 U.S.C. 154(b) by 915 days.

(21) Appl. No.: 17/414,160

(22) PCT Filed: Jan. 3, 2020

(86) PCT No.: PCT/EP2020/050101
§ 371 (c)(1),
(2) Date: Jun. 15, 2021

(87) PCT Pub. No.: WO2020/141226
PCT Pub. Date: Sep. 7, 2020

(65) Prior Publication Data
US 2022/0079959 A1     Mar. 17, 2022

Related U.S. Application Data

(60) Provisional application No. 62/788,306, filed on Jan. 4, 2019.

(51) Int. Cl.
 A61K 31/64    (2006.01)
 A61K 9/08     (2006.01)
 A61K 47/40    (2006.01)

(52) U.S. Cl.
 CPC ........... *A61K 31/64* (2013.01); *A61K 9/08* (2013.01); *A61K 47/40* (2013.01)

(58) Field of Classification Search
 CPC .... A61K 31/64; A61K 47/40; A61K 47/6951; A61K 9/08
 See application file for complete search history.

(56) References Cited

U.S. PATENT DOCUMENTS

| | | | |
|---|---|---|---|
| 4,663,348 A | 5/1987 | Chafetz et al. | |
| 4,698,361 A | 10/1987 | Di Schiena | |
| 5,134,127 A | 7/1992 | Stella et al. | |
| 5,376,645 A | 12/1994 | Stella et al. | |
| 5,633,240 A | 5/1997 | Ranade | |
| 5,814,623 A | 9/1998 | Ranade | |
| 8,241,661 B1 | 8/2012 | Fuisz et al. | |
| 8,282,366 B2 | 10/2012 | Hilber et al. | |
| 8,372,809 B2 | 2/2013 | Unemori et al. | |
| 8,414,532 B2 | 4/2013 | Brandt et al. | |
| 9,884,039 B2 | 2/2018 | Michaels et al. | |
| 10,272,064 B2 | 4/2019 | Michaels et al. | |
| 10,391,105 B2 | 8/2019 | Cashman et al. | |
| 11,246,851 B2 | 2/2022 | Muntendam | |
| 2008/0076828 A1 | 3/2008 | Dalton et al. | |
| 2009/0233951 A1 | 9/2009 | Somberg et al. | |
| 2010/0292268 A1* | 11/2010 | Mosher | A61K 9/08 514/301 |
| 2011/0060280 A1 | 3/2011 | Caffey et al. | |
| 2012/0077829 A1 | 3/2012 | Somberg et al. | |
| 2013/0252932 A1 | 9/2013 | Seward | |
| 2016/0051507 A1 | 2/2016 | Michaels et al. | |
| 2018/0303790 A1 | 10/2018 | Michaels et al. | |
| 2020/0038364 A1 | 2/2020 | Michaels et al. | |
| 2020/0375898 A1* | 12/2020 | Moreau | A61K 47/18 |

FOREIGN PATENT DOCUMENTS

| | | |
|---|---|---|
| CA | 2685331 C | 7/2016 |
| CN | 1477977 A | 2/2004 |
| EP | 080195 A1 | 6/1983 |
| EP | 1078636 A1 | 2/2001 |
| EP | 2581078 B1 | 12/2014 |
| WO | WO-1992021769 A1 | 12/1992 |
| WO | WO-1996006615 A1 | 3/1996 |
| WO | WO-2002038186 A1 | 5/2002 |
| WO | WO-2007050075 A1 | 5/2007 |
| WO | WO-2009140659 A1 | 11/2009 |
| WO | WO-2010030667 A1 | 3/2010 |
| WO | WO-2014165660 A1 | 10/2014 |

OTHER PUBLICATIONS

Scifinder database entry for CAS RN 56211-40-6 (accessed May 14, 2024). (Year: 2024).*
Scifinder database entry for CAS RN 77-86-1 (accessed May 14, 2024). (Year: 2024).*
PubChem entry for Captisol (PubChem CID 66577045); accessed Feb. 14, 2025. (Year: 2025).*
Ammar et al., "Inclusion complexation of furosemide in cyclodextrins: Part 1. Effect of cyclodextrins on the physicochemical characteristics of furosemide," *Pharmazie*,, vol. 54, No. 2, pp. 142-144 (1999).
Captisol Safety Data Sheet, dated Feb. 4, 2016, 2 pages.

(Continued)

*Primary Examiner* — Eric Olson
*Assistant Examiner* — Benjamin M Brandsen
(74) *Attorney, Agent, or Firm* — Dechert LLP

(57) ABSTRACT

A pharmaceutical composition and a method of administering the pharmaceutical composition to a patient suffering from edema, heart failure, kidney or liver disease or having symptoms thereof are disclosed. The pharmaceutical composition includes torsemide, or a pharmaceutically acceptable salt, hydrate or ester thereof and a cyclodextrin.

22 Claims, 1 Drawing Sheet

(56) References Cited

OTHER PUBLICATIONS

El-Shenawy et al., "Enhancement of Solubility and Dissolution Rate of Torsemide as Poorly Soluble Loop Diuretic by Inclusion Complexation with both ß-Cyclodextrin and Hydroxypropyl-ß-Cyclodextrin," *Ijppr. Human*, vol. 7, pp. 221-235 (2016).

Garnero et al., "Improving furosemide polymorphs properties through supramolecular complexes of ß-cyclodextrin," *Journal of Pharmaceutical and Biomedical Analysis*, vol. 95, pp. 139-145 (2014).

International Search Report and Written Opinion of the International Searching Authority, the European Patent Office, for International Application No. PCT/EP2019/084446, dated Mar. 17, 2020, 10 pages.

International Search Report and Written Opinion of the International Searching Authority, the European Patent Office, for International Application No. PCT/EP2020/050098, dated Mar. 25, 2020, 13 pages.

Jain et al., "Sulfobutyl Ether7 β-Cyclodextrin (SBE7 β-CD) Carbamazepine Complex: Preparation, Characterization, Molecular Modeling, and Evaluation of In Vivo Anti-epileptic Activity," *AAPS PharmSciTech*, vol. 12, No. 4, ( 2011).

Ozdemir & Ordu, "Improvement of dissolution properties of furosemide by complexation with beta-cyclodextrin," *Drug Dev Ind Pharm* (1998) vol. 24(1), pp. 19-25 (Abstract only).

Press release entitled "Ligand and SQ Innovation Enter Into Exclusive Wordwide Captisol® License and Supply Agreements for High-Concentration Furosemide Formulation," dated Jul. 8, 2019, 5 pages.

Rowe, R.C., Sheskey, P.J. and Quinn, M.E., Handbook of Pharmaceutical Excipients, 6th Edition, *Pharmaceutical Press*, pp. 210-214 (2009).

Santos et al., "Stability of furosemide and aminophylline in parenteral solutions," *Brazilian Journal of Pharmaceutical Sciences*, vol. 47, pp. 89-96 (2011).

Sica et al., "Subcutaneous Furosemide in Heart Failure," *JACC: Basic to Translational Science*, vol. 3, No. 1, pp. 25-34 (2018).

Spamer et al., "Characterization of the complexes of furosemide with 2-hydroxypropyl-ß-cyclodextrin and sulfobutyl ether-7-ß-cyclodextrin," *European Journal of Pharmaceutical Sciences*, vol. 16, pp. 247-253 (2002).

English language machine translation of CN 1477977 A, retrieved on Jun. 23, 2024 from WIPO at: https://patentscope.wipo.int/search/en/detail.jsf?docId=CN82669587&_cid=P21-LXRUCB-56436-1.

* cited by examiner

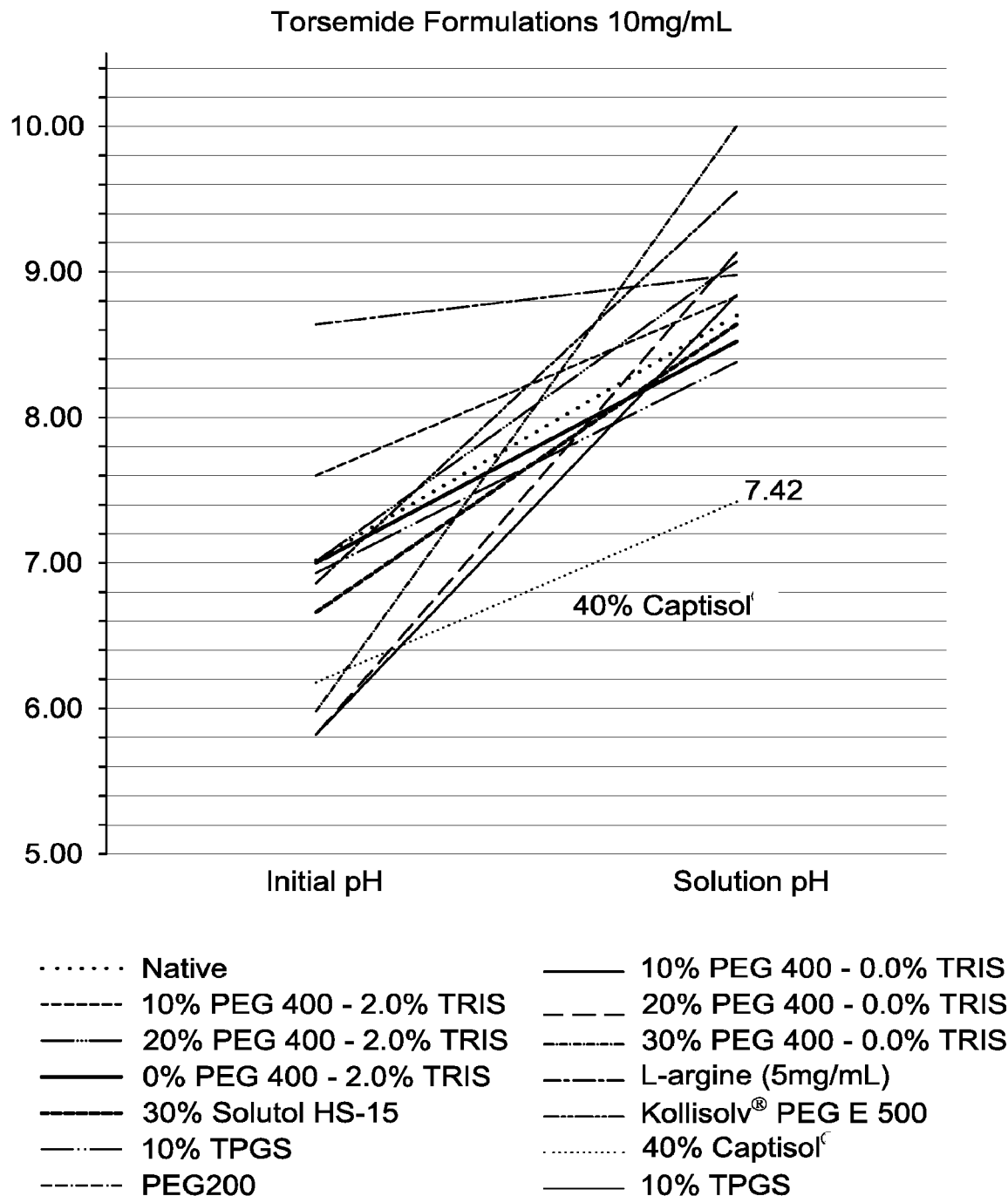

PHARMACEUTICAL COMPOSITIONS OF TORSEMIDE AND USES THEREOF

CROSS-REFERENCE TO RELATED APPLICATIONS

This application is the national stage application of International (PCT) Patent Application Serial No. PCT/EP2020/050101, filed Jan. 3, 2020, which claims the benefit of and priority to U.S. Provisional Patent Application Ser. No. 62/788,306, filed Jan. 4, 2019, the contents of these applications are hereby incorporated by reference in their entirety.

FIELD OF THE INVENTION

The present disclosure relates to pharmaceutical compositions containing torsemide and a cyclodextrin and methods of administering the pharmaceutical compositions to a patient. More specifically, the present disclosure relates to pharmaceutical compositions containing torsemide and a cyclodextrin and uses thereof.

BACKGROUND

Torsemide, or torasemide, is a loop diuretic of the pyridine-sulfonylurea class. Chemically, torsemide is 1-isopropyl-3-((4-m-toluidino-3-pyridyl)sulfonyl)urea. Torsemide is mainly used in the management of edema associated with congestive heart failure, renal failure, hypertension and hepatic diseases. Torsemide has a prolonged duration of action compared to other loop diuretics. Torsemide also has a relatively long half-life and higher bioavailability after oral administration.

However, torsemide is poorly soluble at physiological pH, and sterile pharmaceutical formulations for parenteral administration typically have a pH of 9.0 or higher and contain 10 mg/mL of torsemide. On the other hand, reducing the pH of the formulation results in precipitation of torsemide, impacts the stability of a pharmaceutical formulation, and presents additional challenges.

Furthermore, certain clinical uses are precluded or restricted by a high pH in a pharmaceutical formulation, including subcutaneous administration and use in certain infusion fluids where precipitation may occur.

Therefore, to provide a therapeutic dose of torsemide to a patient by subcutaneous administration, it is necessary for a pharmaceutical composition of torsemide to have higher solubility at physiological pH to reduce drug irritation and effective drug delivery with minimal or negligible adverse toxicological effects.

Thus, a need exists for therapeutically effective improved pharmaceutical compositions containing torsemide at physiological pH.

SUMMARY

The present disclosure provides a pharmaceutical composition containing torsemide or a pharmaceutically acceptable form of the torsemide and a cyclodextrin, or a cyclodextrin derivative. The present disclosure also provides a method of treating a patient suffering from edema, heart failure, kidney or liver disease or having symptoms thereof by administering the pharmaceutical composition containing the torsemide or any such pharmaceutical form of the torsemide and the cyclodextrin or a cyclodextrin derivative.

In one aspect, the present disclosure provides the pharmaceutical composition including the torsemide or a pharmaceutically acceptable salt, hydrate or ester of the torsemide and the cyclodextrin. In an embodiment, the cyclodextrin is a β-cyclodextrin. In an embodiment, the β-cyclodextrin present in the pharmaceutical composition is a sulfobutyl ether derivative of β-cyclodextrin. In another embodiment of the present disclosure, the pharmaceutical composition includes the torsemide and the sulfobutyl ether derivative of β-cyclodextrin. In certain embodiments, the sulfobutyl ether derivative of β-cyclodextrin is captisol. In certain embodiments, the pharmaceutical composition further comprises water, and the molar ratio of cyclodextrin to torsemide is greater than 2.

The present disclosure also provides the pharmaceutical composition including the torsemide or derivatives thereof and a cyclodextrin or cyclodextrin derivatives for administration at a pH value from about 7.0 and about 7.8. In an embodiment, the present disclosure provides the pharmaceutical composition including the torsemide or a pharmaceutically acceptable salt, hydrate or ester thereof, and the cyclodextrin at an amount of less than or equal to 50% of the pharmaceutical composition. In an embodiment, the pharmaceutical composition contains the torsemide at a concentration of from about 2 mg/mL and 20 mg/mL. In an embodiment, the pH value of the pharmaceutical composition is from about 7.0 and about 7.8. In certain embodiments, the pH value of the pharmaceutical composition is from about 7.2 to about 7.6. In some embodiments, the pH value of the pharmaceutical composition is from about 7.2 to about 7.42. In some embodiments, the pH value of the pharmaceutical composition is about 7.42.

In another aspect, the present disclosure provides a method of treating a patient suffering from edema, heart failure, kidney or liver disease or having symptoms thereof. The method includes administering to the patient a therapeutically effective amount of a pharmaceutical composition containing torsemide, or a pharmaceutically acceptable salt, hydrate or ester thereof and a cyclodextrin. In some embodiments, the pharmaceutical composition further comprises water, and the molar ratio of cyclodextrin to torsemide is greater than 2. In some embodiments, the method includes administering from 20 mg to 200 mg of the torsemide. In certain embodiments, the amount of the cyclodextrin is less than or equal to 50% of the pharmaceutical composition. In various embodiments, the method includes administering the pharmaceutical composition at a pH value from about 7.2 and about 7.8. In some embodiments, the method includes administering the pharmaceutical composition at the pH value from about 7.2 and about 7.6. In certain embodiments, the pH value is maintained at about 7.42.

In some embodiments, the present disclosure provides the pharmaceutical composition for subcutaneous administration and intravenous administration. The method further includes administering a therapeutically effective dose of the pharmaceutical composition to the patient using a pump device. The pump device is a patch device for parenteral administration of the composition. In another embodiment, the pharmaceutical composition is administered to the patient using an injection device. The injection device is an auto injector device. In various embodiments, the pharmaceutical composition is administered to the patient subcutaneously or intravenously using the patch device or the auto injector device.

The foregoing as well as other features and advantages of the present disclosure will be more fully understood from the following description, examples, and claims.

BRIEF DESCRIPTION OF THE DRAWINGS

The drawing described below is for illustration purpose only and is not intended to limit the scope of the present disclosure in any way.

FIG. 1 is a graph representing (i) a native torsemide formulation and (ii) torsemide formulations with different excipients.

DETAILED DESCRIPTION

The present disclosure in this application includes multiple illustrations of the invention. A skilled artisan will appreciate that various alternate embodiments and forms may be prepared. Examples, therefore, given are only for illustration purposes without any intention to restrict the embodiments to a given set of examples. Specific functional aspects are provided merely to enable a skilled artisan to perform the invention and should not be construed as limitations of the invention.

The use of the terms "include," "includes," "including," "have," "has," "having," "comprise," "comprises," "comprising" or the like should be generally understood as open-ended and non-limiting unless specifically stated otherwise.

The present disclosure includes pharmaceutical compositions of torsemide and a cyclodextrin and methods of administering the pharmaceutical compositions for treating a patient suffering from edema, heart failure, kidney or liver disease or having such disease symptoms. More specifically, the present disclosure provides the pharmaceutical compositions having the torsemide and a β-cyclodextrin or a derivative of β-cyclodextrin such as a sulfobutyl ether derivative. In certain embodiments, the sulfobutyl ether derivative of β-cyclodextrin is captisol. The cyclodextrin can be at an amount of less than or equal to 50% of the pharmaceutical composition at a pH value from about 7.0 to about 7.8. The pharmaceutical composition is suitable for parenteral administration, more specifically, suitable for subcutaneous and intravenous administration. The pharmaceutical compositions are useful in the treatment of edema, hypertension or heart failure in a patient having or exhibiting symptoms of such conditions.

As used herein, "torsemide" refers to a compound having the formula $C_{16}H_{20}N_4O_3S$ and pharmaceutically acceptable salts, hydrates and esters and any variations thereof, such as torsemide modification I, torsemide modification II, torsemide modification π, torsemide modification IV, torsemide modification H, torsemide modification 13 and any such form, modification, or rearrangement of any polymorphic or amorphous form into other polymorphic or amorphous form of torsemide known in the art. Torsemide can be referred to by other names such as torasemide, N-[[(1-methylethyl)amino]carbonyl]-4-[(3-methylphenyl) amino]-, 1-isopropyl-3-((4-m-toluidino-3-pyridyl)sulfonyl) urea, 3-pyridinesulfonamide or its IUPAC name, N-[(isopropylamino)carbonyl]-[(3-methylphenyl)amino]pyridine-3-sulfonamide or its common trade names such as DEMADEX®, DIUVER®, EXAMIDE™ and Tortas™. It is understood that "torsemide" will further refer to any precursor or metabolite or modified form as may be required for administration or conversion into any such form after administration.

As used herein, "cyclodextrin" refers to cyclic compounds of 5 or more α-D-glucopyranoside units linked by 1,4-glycosidic bonds, or compounds containing glucose monomers ranging from six to eight units in a ring designated as 6 glucose subunits known as α-cyclodextrin, 7 glucose subunits known as β-cyclodextrin and with 8 glucose subunits known as γ-cyclodextrin. In addition, the present disclosure includes cyclodextrin-related compounds, for example, compounds derived from cyclodextrins or structurally-related to cyclodextrins.

As used herein, "CAPTISOL®" refers to the trade name for a proprietary modified mixture of cyclodextrin preparation with a modified structure to optimize the solubility and stability of drugs. CAPTISOL® is a mixture of polyanionic β-cyclodextrin derivatives of a sodium sulfonate salt tethered to the lipophilic cavity of a butyl ether group, or sulfobutyl ether. CAPTISOL® is commercially available from Ligand Pharmaceuticals Inc. located in San Diego, California.

As used herein, the term "captisol" is a mixture of polyanionic β-cyclodextrin derivatives of a sodium sulfonate salt separated from the hydrophobic cavity of the β-cyclodextrin with a butyl ether spacer group. Chemically, captisol is also referred to as sulfobutyl ether beta-cyclodextrin sodium.

As used herein, "derivative" refers to a modified form of a compound generated by various methods or processes including, but not limited to, methylation, acetylation, substitutions such as alkylation, amidation, quaternization, thiolation, sulfation, and oxidation, chain elongations such as cross-linking and grafting, and depolymerization by chemical, physical, or biological including enzymatic means. The methods and processes can be employed either alone or in any combination without any specific order.

As used herein, "preventing or treating" refers to partially or completely alleviating and/or ameliorating the condition and/or symptoms thereof, and/or preventing its re-occurrence or halting its progression. The present disclosure accordingly includes a method of providing to the patient a combination product that includes a compound or therapeutic composition of the present disclosure in combination or association with a pharmaceutically acceptable carrier, solubilizer or an appropriate buffer.

As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

As used herein, "therapeutically effective" refers to a substance or an amount that elicits a desirable biological activity or effect reducing or arresting disease processes. For example, a "therapeutically effective amount" of a composition can deliver a dose (also referred to as a "therapeutic dose") sufficient to elicit the desired biological response. In the present invention, the desired biological response is "treating" of edema, heart failure, kidney or liver disease or having symptoms thereof. As used herein, "treating" refers to partially or completely alleviating and/or ameliorating the condition and/or symptoms thereof.

As used herein, "administration" refers to parenteral including intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion, unless specifically mentioned. Specifically, the pharmaceutical composition of the present disclosure can be administered parenterally including infusion, injection or implantation, which includes subcutaneous and intravenous administration. When administered for the treatment of a disease state or disorder, it is understood that an effective dosage can vary depending upon many factors such as the compound or therapeutic composition utilized, the mode of administration, and severity of the condition being treated, as well as the various physical factors related to the individual being treated. In therapeutic applications, a compound or therapeutic composition of the present disclosure can be provided to a patient already suffering from a disease, for example, edema related disorders, in an amount sufficient to at least partially ameliorate the symptoms of the disease and its complications and halt or slow down the disease progression. If administered to a patient suffering from the condition prior to clinical manifestation, the administration of a therapeutic composition may prevent the first clinical manifestation or delay its onset.

As used herein, "patient" refers to a mammal, such as a human or a domesticated animal such as a pet.

As used herein, the term "about" refers to a ±10% variation from the nominal value unless otherwise indicated or inferred. For example, in certain applications, such as pH measurements, the term "about" can refer to a ±5%, or a ±2.5%, or a ±1% variation from the nominal value or a fixed variation from the nominal value, for example, ±0.1 pH units or ±0.2 pH units.

The present disclosure provides the pharmaceutical compositions that include the torsemide or a therapeutic combination including torsemide, and one or more pharmaceutically acceptable carriers, excipients, or diluents such as a buffer. The excipients may include sodium chloride, sodium hydroxide, water, glycerol, mannitol, sodium phosphate, sodium carbonate, lactose, dextrose and other electrolytes.

Examples of such carriers are well known to skilled artisan and can be prepared in accordance with acceptable pharmaceutical procedures such as, for example, those described in Remington: The Science and Practice of Pharmacy, 20th edition, ed. Alfonso R. Gennaro (Lippincott Williams & Wilkins, Baltimore, MD (2000)). For example, liquid media or liquid carriers (which are used interchangeably herein) can be used in preparing the pharmaceutical compositions of the present disclosure such as solutions, suspensions, and emulsions. A compound described herein can be dissolved or suspended in a pharmaceutically acceptable liquid carrier such as a buffer, an organic solvent, and/or pharmaceutically acceptable oils and/or fats.

The pharmaceutical compositions of the present disclosure can include other suitable pharmaceutical additives such as solubilizers, emulsifiers, buffers, preservatives, suspending agents, thickening agents, colors, viscosity regulators, stabilizers, adsorbents, binders, antioxidants, bulking agents, pH adjusting agents, preservative, solvent, fluidizing agents and osmo-regulators. As the present disclosure provides the pharmaceutical compositions and their intended use is with the patients, each of the ingredients or compounds of the pharmaceutical compositions described herein can be a pharmaceutically acceptable ingredient or compound.

The use of the singular herein includes the plural (and vice versa) unless specifically stated otherwise.

It is understood that the order of steps or order for performing certain actions can be changed so long as the intended result is obtained. Moreover, two or more steps or actions may be conducted simultaneously.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

Pharmaceutical Compositions Containing Torsemide and Methods of Treatment

The present disclosure provides pharmaceutical compositions and methods of treatment with the pharmaceutical composition containing the torsemide and the cyclodextrin or cyclodextrin derivatives for administration to a patient with strikingly higher aqueous solubility at lower pH with enhanced drug stability, reduced drug irritation, and reduced drug incompatibility when used with other infusion formulations.

Cyclodextrins

Cyclodextrins are cyclic carbohydrates that differ from one another by the number of gluco-pyranose units in the structure. The cyclodextrin structure provides a molecule shape like a truncated cone with a hydrophilic exterior surface and hydrophobic interior cavity. These properties make cyclodextrins very valuable for drug administration. The hydrophilic surface provides cyclodextrins with good water solubility and the hydrophobic cavity creates a suitable position to include a drug molecule. A variety of non-covalent forces, such as van der Waals forces, hydrophobic interactions and other forces are responsible for the formation of stable complexes of cyclodextrins and drug molecule. Many processes are used to form cyclodextrin-drug complexes, such as co-precipitation, heating, extrusion, dry mixing, damp mixing, slurry complexation, and paste complexation. Oral uses of the naturally occurring cyclodextrins is well-known with limited parenteral use and applications. Therefore, modified forms of cyclodextrins are generally used in parenteral and other routes of administration for higher stability and bioavailability.

One such modified cyclodextrin is captisol, which is an anionic $\beta$-cyclodextrin derivative with sodium sulfate salt separated from the hydrophobic cavity with a butyl ether spacer group. Parenteral studies with captisol demonstrate a substantially higher safety profile with substantially higher complexation characteristics and water stability greater than 35 times over the parent cyclodextrin.

Pharmaceutical Compositions Containing Torsemide

The present disclosure provides a pharmaceutical composition of the torsemide and the cyclodextrin or derivatives thereof, such as $\beta$-cyclodextrin derivative (e.g., captisol). In certain embodiments, the pharmaceutical composition further comprises water, and the molar ratio of cyclodextrin to torsemide is greater than 2. The route of administration for the pharmaceutical composition can be parenteral, more specifically, subcutaneous and intravenous route. The specific amount of the cyclodextrin is less than or equal to about 50% of the pharmaceutical composition and the pH values achieved from about 7.0 to about 7.8. As such, one advantage of the disclosure is that torsemide can be administered by subcutaneous infusion or injection to the patient in need thereof. Another advantage of the present disclosure is the ability to administer a therapeutic dose of the torsemide such as 80 mg within the standardized volume of a common cartridge used in a patch pump, i.e., 3-5 mL, to the patient using a patch pump.

Yet another advantage of the present disclosure is the ability to administer a therapeutic dose of the torsemide, such as 50 mg, by means of an injection device such as an autoinjector. Yet another advantage of the present disclosure is the use in intravenous infusion when other infusion fluids are used concurrently or sequentially without the need for line flushing before and after administration of torsemide. Yet another advantage of the present disclosure is that the pharmaceutical composition remains stable at the pH value from about 7.0 to about 8.3 and is compatible for subcutaneous or intravenous administration of the torsemide with effective delivery and minimal or negligible adverse toxicological effects.

In one embodiment of the present disclosure, the pharmaceutical composition remains stable at the pH value of from about 7.0 to about 7.8. In certain embodiments of the present disclosure, the pharmaceutical composition remains stable at the pH value from 7.2 to 7.6 for subcutaneous or intravenous administration of torsemide. In certain embodiments, the pharmaceutical composition remains stable at the pH value of 7.42 and is compatible for subcutaneous or intravenous administration of the torsemide with effective delivery and minimal or negligible adverse toxicological effects.

In certain embodiments, another advantage of the present disclosure is that the molar ratio of the cyclodextrin to the torsemide is maintained from 1 to 1.5 in the pharmaceutical composition to reduce the osmolarity as compared to pharmaceutical compositions having a molar ratio of 2 or higher.

The torsemide can be present in the pharmaceutical composition as torsemide or in the form of any variations of analogs such as a pharmaceutically acceptable salt, hydrate or an ester. In some embodiments, the amount of the torsemide in the pharmaceutical composition is from about 2 mg/mL to about 20 mg/mL. In some embodiments, the amount of the torsemide is from about 5 mg/mL to about 20 mg/mL. In some embodiments, the pharmaceutical composition further contains the cyclodextrin or derivatives thereof at an amount of less than or equal to 50% and maintain the pH value of the pharmaceutical composition from about 7.0 to about 7.8.

In certain embodiments, the pH value of the pharmaceutical composition is maintained from about 7.2 to about 7.6. In certain embodiments, the pH value of the pharmaceutical composition is maintained from about 7.2 to about 7.42.

In an embodiment, molar ratio of the cyclodextrin to the torsemide in the pharmaceutical composition is less than or equal to 1.5. In another embodiment, the molar ratio of the cyclodextrin to the torsemide is less than or equal to 0.8. In yet another embodiment, the molar ratio of the cyclodextrin to the torsemide is from about 0.8 and about 1.5. In yet another embodiment, the molar ratio of the cyclodextrin to the torsemide is from about 1 and about 1.5.

In certain embodiments, the amount of the torsemide in the pharmaceutical composition is from about 5 mg/mL to about 20 mg/mL and the cyclodextrin is included in the pharmaceutical composition at an amount less than or equal to 50%. The pH value of the pharmaceutical composition is maintained from about 7.2 to about 7.8 with the molar ratio of the cyclodextrin to the torsemide maintained from about 1 to about 1.5. One advantage of the combination of the ingredients in the disclosed amounts and at the disclosed conditions is that therapeutic dose of the torsemide such as 80 mg can be accommodated within a standard size cartridge of the patch pump, e.g., 3-5 mL, and administered to the patient, or self-administered by the patient using, for example, the patch pump.

In some embodiments, the amount of the torsemide in the pharmaceutical composition is from about 5 mg/mL to about 20 mg/mL. In certain embodiments, the amount of the sulfobutyl ether derivative of β-cyclodextrin (e.g., captisol), in the pharmaceutical composition is less than or equal to 50%. In certain embodiments, the pH value of the pharmaceutical composition is from about 7.0 to about 7.8. In certain embodiments, the molar ratio of the captisol to the torsemide is from about 1 to about 1.5. In yet another embodiment, the above pharmaceutical composition is administered to the patient subcutaneously or intravenously as needed.

In another aspect, the present disclosure provides a pharmaceutical composition comprising:
  from about 14 mM to about 115 mM of a diuretic selected from the group consisting of N-(isopropylcarbamoyl)-4-(m-tolylamino)pyridine-3-sulfonamide, a pharmaceutically acceptable salt thereof, and a mixture of the foregoing;
  from about 45 mM to about 190 mM of a sulfobutyl ether derivative of β-cyclodextrin; and
  water; wherein the pharmaceutical composition has a pH value from about 7.0 to about 8.0.

The pharmaceutical composition can be further characterized according to the amount of sulfobutyl ether derivative of β-cyclodextrin. For example, in certain embodiments, the pharmaceutical composition comprises from about 90 mM to about 140 mM of a sulfobutyl ether derivative of β-cyclodextrin. In certain embodiments, the pharmaceutical composition comprises from about 80 mM to about 100 mM of a sulfobutyl ether derivative of β-cyclodextrin. In certain embodiments, the pharmaceutical composition comprises from about 130 mM to about 150 mM of a sulfobutyl ether derivative of β-cyclodextrin. In certain embodiments, the sulfobutyl ether derivative of β-cyclodextrin is sulfobutyl ether beta-cyclodextrin sodium.

The pharmaceutical composition can be further characterized according to the amount of diuretic. For example, in certain embodiments, the pharmaceutical composition comprises from about 25 mM to about 60 mM of the diuretic. In certain embodiments, the pharmaceutical composition comprises from about 25 mM to about 30 mM of the diuretic. In certain embodiments, the pharmaceutical composition comprises from about 55 mM to about 60 mM of the diuretic.

In certain embodiments, the pharmaceutical composition further comprises a buffer. In certain embodiments, the buffer comprises tris(hydroxymethyl)aminomethane.

In certain embodiments, the buffer is present in an amount ranging from about 1% (w/w) to about 5% (w/w). In certain embodiments, the buffer is present in an amount of about 2% (w/w).

In certain embodiments, the pharmaceutical composition has a pH of from about 7.2 to about 7.6. In certain embodiments, the pharmaceutical composition has a pH of about 7.4.

In certain embodiments, the pharmaceutical composition contains at least 95% (w/w) water.

The pharmaceutical composition of the present disclosure contains the torsemide with high solubility and enhanced stability, which advantageously enables administration of a higher dose of the torsemide in lower volume of the pharmaceutical composition. The pharmaceutical composition of the present disclosure achieves the administration of the higher concentration of the torsemide at a pH value that is compatible for subcutaneous administration to the patient. More specifically, the pharmaceutical composition is stable and suitable for subcutaneous or intravenous administration.

In some embodiments, the present disclosure includes the pharmaceutical composition of the torsemide at a higher concentration in a drug volume of 2-20 mL. In another embodiment, the amount of the cyclodextrin in the pharmaceutical composition is less than or equal to 50%. In yet another embodiment, the pharmaceutical composition has the pH value from about 7.0 to about 7.8 compatible for subcutaneous and intravenous administration.

In some embodiments, the present disclosure includes the pharmaceutical composition of the torsemide and the cyclodextrin or cyclodextrin derivative, such as captisol, at an amount from about 40% to about 50%.

Methods of Treatment

In another embodiment, the present disclosure includes a method of treating the patient with or exhibiting symptoms of edema, heart failure, kidney or liver disease by administering to the patient the pharmaceutical composition containing torsemide, or the pharmaceutically acceptable salt, hydrate or ester thereof. More particularly, the pharmaceutical composition contains torsemide, or the pharmaceutically acceptable salt, hydrate or ester thereof at a concentration of about 20 mg/mL. In certain embodiments, the pharmaceutical composition further contains the cyclodextrin at an amount of less than or equal to 50% in the pharmaceutical composition.

In another embodiment, the present disclosure provides a method of treating a patient suffering from a condition selected from edema, heart failure, kidney disease, or liver disease, or having a symptom any of the foregoing, wherein the method comprises administering to the patient in need thereof a therapeutically effective amount of a pharmaceutical composition described herein to treat the condition.

In certain embodiments, the condition is edema. In certain embodiments, the condition is heart failure. In certain embodiments, the condition is kidney disease or liver disease.

In one embodiment, the pharmaceutical composition is administered to the patient subcutaneously. Specifically, the pharmaceutical composition is administered to the patient subcutaneously using a pump device or an injection device. The pump device can include, for example, a patch device. The injection device can include, for example, an auto injector device. In another embodiment, the pharmaceutical composition is administered to the patient intravenously. Specifically, the pharmaceutical composition is administered to the patient intravenously using the pump device or the injection device. In various embodiments, the pharmaceutical composition is administered to the patient subcutaneously or intravenously using the patch device or the auto injector device.

In some embodiments, a method of treating the patient with or exhibiting symptoms of edema, heart failure, kidney or liver disease comprises administering to the patient the pharmaceutical composition of torsemide, or the pharmaceutically acceptable salt, hydrate or torsemide ester with an amount of the torsemide in the pharmaceutical composition to about 20 mg/mL. In certain embodiments, the pharmaceutical composition further contains the cyclodextrin or derivatives thereof at an amount of less than or equal to 50% at the pH value of the pharmaceutical composition from about 7.2 and about 7.6. In one embodiment, the cyclodextrin is a β-cyclodextrin. In another embodiment the cyclodextrin is a sulfobutyl ether derivative of β-cyclodextrin. In yet another embodiment, the sulfobutyl ether derivative of β-cyclodextrin is captisol. In one embodiment, the pH value of the pharmaceutical composition is from about 7.0 to about 7.8. In certain embodiments, the pH value is maintained from about 7.0 to about 8.3.

In an embodiment, the patient suffering from edema, heart failure, kidney or liver disease or exhibiting such symptoms thereof is administered the pharmaceutical composition with the amount of the torsemide from about 5 mg/mL to about 20 mg/mL. In another embodiment, the amount of the captisol in the pharmaceutical composition is less than or equal to 50%. In another embodiment, the pH of the pharmaceutical composition is from about 7.0 to about 7.8. In yet another embodiment, the molar ratio of the captisol to the torsemide is from about 1 to about 1.5.

In some embodiments, the pharmaceutical composition is administered to the patient parenterally including subcutaneous or intravenous administration. In the present disclosure, several devices can be used to facilitate self-administration of the pharmaceutical composition. The device typically includes a reservoir or a cartridge, for example, pre-loaded with the pharmaceutical composition to be administered. For example, a micropump can provide precise parenteral administration of desired quantities of a liquid pharmaceutical composition. Another type of device useful for parenteral delivery or administration of pharmaceutical composition is often referred to as the pump device or the injection device.

In some embodiments, the present disclosure includes medical devices of a unitary construction. Such medical devices can be for a single use. In certain embodiments, the medical device can be of a multi-piece construction. In such medical devices, a disposable or a reusable portion or component can be present. For example, a housing defining or including the reservoir can be a disposable or a reusable component of the medical device.

The patch pump or patch device of the present disclosure may include a pump device having a drug reservoir and electrolytically, manually, mechanically, automatically or electronically driven piston. The drug pump device may be furnished with a prefilled cartridge. If a glass cartridge or cartridge of other suitable pharmaceutical-grade composite material is used, the drugs can be stored in the pump device for long-term shelf life. The drug pump device may be implantable, include an adhesive patch for adhesion to patient's skin, or maybe worn on a belt or is attached to the body by a strap or by other means.

Additional Features of Pharmaceutical Compositions and Methods of Treatment

The pharmaceutical forms of the present disclosure suitable for injection can include sterile aqueous solutions and dispersions for the extemporaneous preparation of sterile injectable solutions or dispersions. In certain embodiments, the pharmaceutical form is sterile, and its viscosity permits it to flow through a syringe. The pharmaceutical form should be stable under the conditions of manufacture and storage, for example, preserved against the contaminating action of microorganisms, if needed. The carrier can be a solvent or dispersion medium containing liquids such as water, ethanol, polyol (for example, glycerol, propylene glycol, and liquid polyethylene glycol), suitable mixtures thereof, and vegetable oils.

In the present disclosure, the pharmaceutical compositions can achieve higher level of the torsemide suitable for administration. For example, the amount of the torsemide in the pharmaceutical composition can be about 5 mg/mL or greater, about 8 mg/mL or greater, or about 10 mg/mL or greater. In various embodiments, the amount of the torsemide can be about 15 mg/mL or greater, about 10 mg/mL or greater, about 20 mg/mL or greater, or about 20 mg/mL, or about 22 mg/mL or about 23 mg/mL or greater.

Concentration of Torsemide

In some embodiments, the torsemide can be present in an amount from about 2 mg/mL to about 20 mg/mL, from about 10 mg/mL to about 24 mg/mL, from about 10 mg/mL to about 20 mg/mL, from about 10 mg/mL to about 15 mg/mL, from about 15 mg/mL to about 24 mg/mL, from about 16 mg/mL to about 24 mg/mL, or from about 20 mg/mL to about 24 mg/mL.

Disorders for Treatment

In the present disclosure, torsemide, therapeutic combinations, and pharmaceutical compositions can be useful for treating a pathological condition or disorder or symptoms in the patient. The present disclosure provides administering higher concentrations of the torsemide parenterally to alleviate the disorders, such as edema, heart failure, kidney or liver disease or having such symptoms. The present disclosure accordingly includes the method of providing to the patient the pharmaceutical composition that includes a compound or therapeutic combination of the present teachings in combination or association with a pharmaceutically acceptable carrier or solubilizer or a suitable buffer. Compounds and therapeutic combinations of the present disclosure can be administered alone or in combination with other therapeutically effective compounds or therapies for the treatment of a pathological condition or disorder.

The present disclosure also includes the methods of administration of the pharmaceutical composition including the torsemide or one or more of its analogues or variations or precursors to the patient with edema related disease or disorder. The edema related disease or disorder may also include heart failure, chronic kidney disease.

pH of Pharmaceutical Compositions

In certain embodiments, the pharmaceutical composition can have a pH value in the range of about 7.0 to about 8.3. In certain embodiments, the pharmaceutical formulations can have the pH value in the range of about 7.2 to about 7.8, or about 7.2 to about 7.6, or about 7.3 to about 7.8. In some embodiments, the pharmaceutical composition can have the pH value in the range of about 7.4 to about 8.0, or about 8.4 to about 9.6.

Amount of Cyclodextrin

In various embodiments, the molar ratio of the cyclodextrin to the torsemide in the pharmaceutical composition can be greater than about 0.5, or greater than about 0.65, or greater than about 2, or greater than about 1.5, or greater than about 3. In certain embodiments, the molar ratio of the cyclodextrin to the torsemide can be less than or equal to about 0.8, or from about 1.0 to about 1.5. In certain other embodiments, the molar ratio of cyclodextrin to torsemide is from 2:1 to about 15:1. In certain other embodiments, the molar ratio of cyclodextrin to torsemide is from 2:1 to about 3:1.

Further, in various embodiments, the cyclodextrin in the pharmaceutical composition can be less than or equal to about 50%. In some embodiments, the cyclodextrin in the pharmaceutical composition can be less than or equal to about 50%. In some embodiments, the amount of the cyclodextrin can be less than or equal to about 35%, less than or equal to about 30%, or less than or equal to about 25%. In certain embodiments, the amount of the cyclodextrin can be in a range of about 5% to about 50%, about 40% to about 50%, about 20% to about 40%, or about 20% to about 30%. In certain embodiments, the amount of the cyclodextrin can be about 10% or about 40%.

Further, in certain embodiments, the cyclodextrin in the pharmaceutical composition can be less than or equal to about 45% (w/w). In some embodiments, the cyclodextrin in the pharmaceutical composition can be less than or equal to about 40% (w/w). In some embodiments, the amount of the cyclodextrin can be less than or equal to about 35%, less than or equal to about 20% (w/w), or less than or equal to about 15% (w/w). In certain embodiments, the amount of the cyclodextrin can be in a range of about 10% (w/w) to about 50% (w/w), about 35% (w/w) to about 50% (w/w), about 25% (w/w) to about 40% (w/w), or about 25% (w/w) to about 30% (w/w). In certain embodiments, the amount of the cyclodextrin can be about 15% (w/w) or about 45% (w/w).

Therapeutic Benefits

In the present disclosure, the pharmaceutical composition may reduce the disease condition and symptoms by at least about 5% to at least about 99% as compared to an untreated patient. The compound may be administered to the patients in various forms including, an injection, a transdermal patch, and sustained-release formulations. The composition may be administered via enteral or parenteral route including, intravenous, subcutaneous, topical, transdermal, intradermal, transmucosal, intraperitoneal, intramuscular, intracapsular, intraorbital, intracardiac, transtracheal, subcuticular, intraarticular, subcapsular, subarachnoid, intraspinal, epidural and intrasternal injection and infusion.

The typical dosages of the compounds and the compositions of the present disclosure may vary within a wide range depending on many factors, including but not limited to, route of administration, treatment stage, pretreatment use of oral medications, body weight, age and general condition of the patient.

Amount of Water in the Pharmaceutical Composition

The pharmaceutical composition may be further characterized according to the amount of water in the pharmaceutical composition. In certain embodiments, pharmaceutical composition comprises at least 40% (w/w), 45% (w/w), 50% (w/w), 55% (w/w), 60% (w/w), 65% (w/w), 70% (w/w), 75% (w/w), 80% (w/w), or 85% (w/w) water. In certain embodiments, pharmaceutical composition comprises at least 90% (w/w), 91% (w/w), 92% (w/w), 93% (w/w), 94% (w/w), 95% (w/w), 96% (w/w), 97% (w/w), 98% (w/w), or 99% (w/w) water. In certain embodiments, pharmaceutical composition comprises at least 50% (w/w). In certain embodiments, pharmaceutical composition comprises at least 55% (w/w). In certain embodiments, pharmaceutical composition comprises at least 60% (w/w). In certain embodiments, pharmaceutical composition comprises at least 65% (w/w). In certain embodiments, pharmaceutical composition comprises at least 95% (w/w) water. In certain embodiments, pharmaceutical composition comprises at least 96% (w/w) water. In certain embodiments, pharmaceutical composition comprises at least 97% (w/w) water. In certain embodiments, pharmaceutical composition comprises at least 98% (w/w) water. In certain embodiments, pharmaceutical composition comprises at least 99% (w/w) water. In certain embodiments, the pharmaceutical composition comprises from about 50% (w/w) to about 70% (w/w) water. In certain embodiments, the pharmaceutical composition comprises from about 60% (w/w) to about 70% (w/w) water.

Additional Components of the Pharmaceutical Composition

The pharmaceutical composition of the present disclosure may also contain adjuvants, diluents, excipients and/or carriers, known in the art, compatible with the compounds and the other ingredients of the pharmaceutical composition, and not deleterious to the recipient thereof.

Stability of the Pharmaceutical Compositions

The pharmaceutical composition may be further characterized according to stability of the pharmaceutical composition to storage. This can be achieved by storing a pharmaceutical composition at a designated temperature for a duration of time, then removing an aliquot of the pharmaceutical composition, and analyzing the aliquot to determine if any components in the original pharmaceutical composition have degraded. For example, the aliquot can be subjected to visual analysis to determine the presence of any undissolved solids and/or a change in color or clarity of the solution. Also, the aliquot can be analyzed to determine the amount of diuretic present (e.g., torsemide or a pharmaceutically acceptable salt thereof) relative to the original amount of diuretic in the pharmaceutical composition.

Accordingly, in certain embodiments, less than 4% of the diuretic degrades upon storage of the pharmaceutical composition at 40° C. for 29 days. In certain embodiments, less than 1% of the diuretic degrades upon storage of the pharmaceutical composition at 40° C. for 29 days. In certain embodiments, less than 0.5% of the diuretic degrades upon storage of the pharmaceutical composition at 40° C. for 29 days. In certain embodiments, less than 0.1% of the diuretic degrades upon storage of the pharmaceutical composition at 40° C. for 29 days. In certain embodiments, less than 10% of the diuretic degrades upon storage of the pharmaceutical composition at 70° C. for 29 days. In certain embodiments, less than 7% of the diuretic degrades upon storage of the pharmaceutical composition at 70° C. for 29 days. In certain embodiments, less than 5% of the diuretic degrades upon storage of the pharmaceutical composition at 70° C. for 29 days. In certain embodiments, less than 3% of the diuretic degrades upon storage of the pharmaceutical composition at 70° C. for 29 days. In certain embodiments, less than 1% of the diuretic degrades upon storage of the pharmaceutical composition at 70° C. for 29 days. In certain embodiments, less than 3% of the diuretic degrades upon storage of the pharmaceutical composition at 25° C. for 24 months. In certain embodiments, less than 2% of the diuretic degrades upon storage of the pharmaceutical composition at 25° C. for 24 months. In certain embodiments, less than 1% of the diuretic degrades upon storage of the pharmaceutical composition at 25° C. for 24 months. In certain embodiments, less than 0.5% of the diuretic degrades upon storage of the pharmaceutical composition at 25° C. for 24 months. In certain embodiments, less than 0.1% of the diuretic degrades upon storage of the pharmaceutical composition at 25° C. for 24 months. In certain embodiments, less than 0.05% of the diuretic degrades upon storage of the pharmaceutical composition at 25° C. for 24 months.

Additionally, in certain embodiments, the pharmaceutical composition is characterized by the purity of the diuretic in the pharmaceutical composition upon storage. For example, in certain embodiments, the after storage of the pharmaceutical composition at 40° C. for 29 days the diuretic has a purity of at least 97%. In certain embodiments, after storage of the pharmaceutical composition at 40° C. for 29 days the diuretic has a purity of at least 98%. In certain embodiments, after storage of the pharmaceutical composition at 40° C. for 29 days the diuretic has a purity of at least 99%. In certain embodiments, after storage of the pharmaceutical composition at 40° C. for 29 days the diuretic has a purity of at least 99.5%. In certain embodiments, after storage of the pharmaceutical composition at 40° C. for 29 days the diuretic has a purity of at least 99.9%. In certain embodiments, the after storage of the pharmaceutical composition at 70° C. for 29 days the diuretic has a purity of at least 95%. In certain embodiments, after storage of the pharmaceutical composition at 70° C. for 29 days the diuretic has a purity of at least 97%. In certain embodiments, after storage of the pharmaceutical composition at 70° C. for 29 days the diuretic has a purity of at least 98%. In certain embodiments, after storage of the pharmaceutical composition at 70° C. for 29 days the diuretic has a purity of at least 99%. In certain embodiments, after storage of the pharmaceutical composition at 70° C. for 29 days the diuretic has a purity of at least 99.5%. In certain embodiments, the after storage of the pharmaceutical composition at 25° C. for 24 months the diuretic has a purity of at least 97%. In certain embodiments, after storage of the pharmaceutical composition at 25° C. for 24 months the diuretic has a purity of at least 98%. In certain embodiments, after storage of the pharmaceutical composition at 25° C. for 24 months the diuretic has a purity of at least 99%. In certain embodiments, after storage of the pharmaceutical composition at 25° C. for 24 months the diuretic has a purity of at least 99.5%. In certain embodiments, after storage of the pharmaceutical composition at 25° C. for 24 months the diuretic has a purity of at least 99.9%.

Exemplary Benefits of the Pharmaceutical Compositions

Various embodiments of the present disclosure enable administration of higher concentrations of the torsemide to the patient. Further, the pharmaceutical composition of various embodiments of the present disclosure has the pH appropriate for subcutaneous or intravenous administration of the composition to the patient.

Another advantage of the embodiments of the present disclosure is that the pharmaceutical compositions with higher concentration of the torsemide and lower amount of the captisol can be administered with the pump device or the injection device.

Yet another advantage of the pharmaceutical compositions of the present disclosure is substantially high solubility at a desired pH, which may facilitate intravenous infusion by allowing co-administration with other infusion fluids or pharmaceutical formulations.

It has been observed that the torsemide demonstrates higher solubility and enhanced stability in pharmaceutical compositions in combination with the cyclodextrins or cyclodextrin derivatives such as sulfobutyl ether derivative of β-cyclodextrin compared to other excipients with the torsemide for treatment of edema, hypertension, and other renal diseases.

Unit Container

Another aspect of the disclosure provides a unit container comprising a pharmaceutical composition described herein. In certain embodiments, the container contains from about 1 mL to about 10 mL, from about 1 mL to about 5 mL, from about 1 mL to about 4 mL, from about 1 mL to about 3 mL, from about 1 mL to about 2 mL, from about 1 mL to about 1.5 mL, from about 2 mL to about 5 mL, or from about 2 mL to about 3 mL of pharmaceutical composition. In certain embodiments, the container contains from about 1 mL to about 3 mL of pharmaceutical composition. In certain embodiments, the container contains from about 2 mL to about 3 mL of pharmaceutical composition. In certain embodiments, the container contains from about 5 mL to about 10 mL of pharmaceutical composition. In certain embodiments, the container contains from about 8 mL to about 10 mL of pharmaceutical composition.

Medical Kits

Another aspect of the invention provides a medical kit comprising, for example, (i) a pharmaceutical composition described herein, and (ii) instructions for use, such as for use in a method described herein.

It is understood that the examples, embodiments and teachings presented in this application are described merely for illustrative purposes. Any variations or modifications thereof are to be included within the scope of the present application as discussed.

EXAMPLES

The invention now being generally described, will be more readily understood by reference to the following examples, which are included merely for purposes of illustration of certain aspects and embodiments of the present invention, and are not intended to limit the invention.

Example 1: Formulation Prepared with KOLLISOLV® PEG E 400 at 30 Vol. % Concentration To measure the solubility of the torsemide with Polyethylene glycol (PEG), approximately 100.0+/−0.5 mg of torsemide and approximately 2.0 mg of tris(hydroxymethyl) aminomethane (TRIS) (2 wt. %) are weighed into 20 mL clear vial. In a 10 mL volumetric flask, 3379+/−2.0 mg of KOLLISOLV® PEG E 400=1.126 g/mL at 20° C. (purchased from Sigma-Aldrich) is added and then diluted to the volume with Milli-Q water. The KOLLISOLV® PEG E 400 solution is mixed well and then transferred into the above vial containing torsemide and TRIS. The formulation solution is allowed to stir at 20° C., at 1300 rpm for 30 minutes or longer prior to any visual examination and pH measurement. If a suspension is observed, 1.0 N NaOH solution (purchased from EMD Millipore Corporation) is added in small increments each time until a clear solution is obtained. The pH of each solution after NaOH addition was measured for solubility estimate as provided in the Table 1.

TABLE 1

Appearance and pH of Formulation with KOLLISOLV ® PEG E 400 with NaOH Addition

| Experiment (with KOLLISOLV ® PEG E 400) | Volume NaOH Solution Added (µL) | Time Stirred at 20° C. (minutes) | Final pH |
| --- | --- | --- | --- |
| 1-initial | 0 | 30 | 6.86 |
| 2 | +100 | 30 | 7.67 |
| 3 | +100 | 30 | 7.89 |
| 4 | +50 | 30 | 7.95 |
| 5 | +50 | 30 | 8.19 |
| 6 | +30 | 70 | 8.31 |
| 7 | +20 | 60 | 9.55 |
| Overall | 350 | Total of ~4.75 hours | 9.55 |

Example 2: Formulation Prepared with TPGS at 10 Vol. % Concentration

To measure the solubility of the torsemide with Tocophersolan (TPGS), approximately 100.0+/−0.5 mg of torsemide and approximately 2.0 mg of TRIS (2 wt. %) are weighed into 20 mL clear vial. In a 10 mL volumetric flask, 1001.3+/−2.0 mg of TPGS (1.002 g/mL at 25° C., purchased from Sigma-Aldrich) is added and then diluted to the volume with Milli-Q water. The TPGS solution is mixed well and then transferred into the vial containing the torsemide and the TRIS. The formulation solution is allowed to stir at 20° C. at 1300 rpm for 10 minutes or longer prior to any visual examination and pH measurement. If a suspension is observed, 1.0 N NaOH solution (purchased from EMD Millipore Corporation) is added in small increments each time until a clear solution is obtained. The pH of each solution after NaOH addition was measured for solubility estimate as provided in the Table 2.

TABLE 2

Appearance and pH of Formulation with TPGS with NaOH Addition

| Experiment (with TPGS) | Volume of NaOH Solution Added (µL) | Time Stirred at 20° C. (minutes) | Final pH |
| --- | --- | --- | --- |
| 1-initial | 0 | 30 | 6.93 |
| 2 | +150 | 60 | 8.02 |
| 3 | +100 | 30 | 8.27 |
| 4 | +40 | 30 | 8.40 |
| 5 | +20 | 60 | 8.48 |
| 7 | +0 | ~17 hours | 8.38 |
| Overall | 310 | Total of ~20.5 hours | 8.38 |

Example 3: Torsemide Formulation Prepared with Captisol at 40 Wt. % Concentration To measure the solubility of the torsemide with captisol, approximately 100.2+/−0.5 mg of torsemide and approximately 2.0 mg of TRIS (2 wt. %) are weighed into 20 mL clear vial. In a 10 mL volumetric flask, 4002.3+/−2.0 mg of captisol (purchased from Combi-Blocks Incorporation under the tradename CAPTISOL®) is added and then diluted to the volume with Milli-Q water. The captisol solution is mixed well and then transferred into the vial containing the torsemide and the TRIS. The formulation solution is allowed to stir at 20° C. at 1300 rpm for 10 minutes or longer prior to any visual examination and pH measurement. If a suspension is observed, 1.0 N NaOH solution (purchased from EMD Millipore Corporation) is added in small increments each time until a clear solution is obtained. The pH of each solution after NaOH solution addition was measured for solubility estimate as provided in the Table 3.

TABLE 3

Appearance and pH of formulation with captisol with NaOH addition

| Experiment (with captisol) | Volume of NaOH Solution Added (µL) | Time Stirred at 20° C. (minutes) | Final pH |
| --- | --- | --- | --- |
| 1-initial | 0 | 30 | 6.18 |
| 2 | +150 | 60 | 7.07 |
| 3 | +100 | 30 | 7.32 |
| 4 | +40 | 30 | 7.61 |
| 5 | +0 | 960 (16 hours) | 7.40 |
| 6 | +10 | 120 | 7.42 |
| Overall | 300 | Total of ~20.5 hours | 7.42 |

The above experiments demonstrate the solubility of the torsemide in various compositions. More specifically, injection formulation of torsemide at 10 mg/mL and 2% TRIS with excipient of KOLLISOLV® PEG E 400, TPGS and captisol. The above experiments show that the final pH for KOLLISOLV® PEG E 400 formulation (30 vol %) obtained is 9.55 and for TPGS formulation (10 vol %) the pH value obtained is 8.38, which indicates that both the formulations are incompatible for administration and the pH value is higher than physiological value and required value of 8.38.

It is evident from the Table 3 that the unexpected results are demonstrated for torsemide formulation with captisol. The final pH for captisol formulation (40 wt. %) obtained is 7.42 which is compatible for administration and within the physiologically desired value for patient safety.

The above solubility results of torsemide formulation with various expedients demonstrate that the torsemide captisol formulation has an unexpectedly high compatibility for torsemide pharmaceutical composition for administration to a patient in need thereof.

Example 4: Additional Torsemide Formulations

In addition to the above Examples, and in to further support the highly unexpected results obtained with captisol, further studies were conducted to measure the solubility of torsemide with a variety of excipients including captisol as represented in the graph of FIG. 1.

As evident from the graph in FIG. 1, the experiment included various formulations containing different excipient along with torsemide (10 mg/mL) including: PEG 400 (10 wt. %) with TRIS 2.0%, PEG 400 (20 wt. %) with TRIS 2.0%, PEG 400 (0 wt. %) with TRIS 2.0%, Solutol (30 wt. %) HS-15, TPGS (10 wt. %), PEG 200, PEG 400 (10 wt. %) with TRIS 0.0%, PEG 400 (20 wt. %) with TRIS 0.0%, PEG 400 (30 wt. %) with TRIS 0.0%, L-arginine (5 mg/mL), KOLLISOLV® PEG E 500, captisol (40 wt. %), and TPGS (10 wt. %).

The comparison graphically represented in FIG. 1 of buffered and non-buffered formulations establishes the stability and solubility of torsemide with captisol as compared to the other excipients and native formulation. It is evident that maximum solubility of formulation of torsemide at 10 mg/mL with captisol formulation (40 wt. %) is obtained at pH 7.42 which is compatible for administration and within the physiologically desired value. Other excipients used in the experiments, as shown by respective peaks in the graph of FIG. 1, require a much higher pH for solubility with PEG 400 (30 wt. %) with TRIS 0.0% reaching a pH value of 10.

These results further establish the utility of captisol as a physiologically desired excipient for preparing the torsemide formulation for administration to the patient suffering from edema associated with congestive heart failure, renal failure, hypertension and hepatic diseases.

It is understood that the examples, embodiments and teachings presented in this application are described merely for illustrative purposes. Any variations or modifications thereof are to be included within the scope of the present application as discussed.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition, comprising:
   torsemide, or a pharmaceutically acceptable salt, hydrate or ester thereof;
   from 20% to 40% by weight of a β-cyclodextrin;
   a buffer comprising tris(hydroxymethyl)aminomethane; and
   at least 55% (w/w) water;
   wherein the molar ratio of β-cyclodextrin to torsemide is greater than 2; and
   the pharmaceutical composition has a pH value from about 7.0 to about 7.8.

2. The pharmaceutical composition of claim 1, wherein the β-cyclodextrin is a sulfobutyl ether derivative of β-cyclodextrin.

3. The pharmaceutical composition of claim 2, wherein the sulfobutyl ether derivative of β-cyclodextrin is sulfobutyl ether beta-cyclodextrin sodium.

4. The pharmaceutical composition of claim 1, wherein the pharmaceutical composition has a pH value from about 7.2 to about 7.6.

5. The pharmaceutical composition of claim 1, wherein the pharmaceutical composition has a pH value of about 7.42.

6. The pharmaceutical composition of claim 1, wherein the pharmaceutical composition contains the torsemide in an amount of from about 10 mg/mL to about 20 mg/mL.

7. The pharmaceutical composition of claim 6, wherein the pharmaceutical composition contains the β-cyclodextrin in an amount of from 20% to 30% by weight.

8. The pharmaceutical composition of claim 7, wherein the water is present in an amount of at least 60% (w/w) of the pharmaceutical composition.

9. The pharmaceutical composition of claim 1, wherein the molar ratio of β-cyclodextrin to torsemide is from 2:1 to about 3:1.

10. A pharmaceutical composition, comprising:
    from about 14 mM to about 115 mM of a diuretic selected from the group consisting of N-(isopropylcarbamoyl)-4-(m-tolylamino)pyridine-3-sulfonamide, a pharmaceutically acceptable salt thereof, and a mixture of the foregoing;
    from 90 mM to 140 mM of a sulfobutyl ether derivative of β-cyclodextrin;
    a buffer comprising tris(hydroxymethyl)aminomethane; and
    at least 60% (w/w) water; wherein the pharmaceutical composition has a pH value from about 7.0 to about 8.0.

11. The pharmaceutical composition of claim 10, wherein the sulfobutyl ether derivative of β-cyclodextrin is sulfobutyl ether beta-cyclodextrin sodium.

12. The pharmaceutical composition of claim 10, wherein the pharmaceutical composition comprises from about 25 mM to about 60 mM of the diuretic.

13. The pharmaceutical composition of claim 10, wherein the pharmaceutical composition comprises from about 25 mM to about 30 mM of the diuretic.

14. The pharmaceutical composition of claim 10, wherein the pharmaceutical composition comprises from about 55 mM to about 60 mM of the diuretic.

15. The pharmaceutical composition of claim 10, wherein the buffer is present in an amount ranging from about 1% (w/w) to about 5% (w/w).

16. The pharmaceutical composition of claim 10, wherein the buffer is present in an amount of about 2% (w/w).

17. The pharmaceutical composition of claim 10, wherein the pharmaceutical composition has a pH of from about 7.2 to about 7.6.

18. The pharmaceutical composition of claim 10, wherein the pharmaceutical composition has a pH of about 7.4.

19. The pharmaceutical composition of claim 10, wherein less than 1% of the diuretic degrades upon storage of the pharmaceutical composition at 40° C. for 29 days.

20. A method of treating a patient suffering from a condition selected from edema, heart failure, kidney disease, or liver disease, or having a symptom of any of the foregoing, comprising administering to the patient in need thereof a therapeutically effective amount of a pharmaceutical composition of claim 10 to treat the condition.

21. A pharmaceutical composition, comprising:
- from about 14 mM to about 115 mM of a diuretic selected from the group consisting of N-(isopropylcarbamoyl)-4-(m-tolylamino)pyridine-3-sulfonamide, a pharmaceutically acceptable salt thereof, and a mixture of the foregoing;
- from about 130 mM to about 150 mM of a sulfobutyl ether derivative of β-cyclodextrin;
- a buffer comprising tris(hydroxymethyl)aminomethane; and
- at least 55% (w/w) water; wherein the pharmaceutical composition has a pH value from about 7.0 to about 8.0.

22. The pharmaceutical composition of claim 21, wherein the water is present in an amount of at least 60% (w/w) of the pharmaceutical composition.

* * * * *